US00PP18682P2

(12) United States Plant Patent
Miedema-Jorna

(10) Patent No.: US PP18,682 P2
(45) Date of Patent: Apr. 1, 2008

(54) **NEW GUINEA *IMPATIENS* PLANT NAMED 'TAMAR ORANGE ORCHID'**

(50) Latin Name: *Impatiens hawkeri*
Varietal Denomination: Tamar Orange Orchid

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 11/637,861

(22) Filed: Dec. 12, 2006

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
(74) *Attorney, Agent, or Firm*—C. A. Whealy

(57) ABSTRACT

A new and distinct cultivar of *Impatiens* plant named 'Tamar Orange Orchid', characterized by its upright and outwardly spreading growth habit; mounded plant form; freely branching habit; dark green-colored leaves; freely flowering habit; large dark orange and light pink bi-colored flowers; and good garden performance.

2 Drawing Sheets

Botanical designation: *Impatiens hawkeri.*

Cultivar denomination: 'Tamar Orange Orchid'.

BACKGROUND OF THE INVENTION

The present invention relates to a new and distinct cultivar of New Guinea *Impatiens,* botanically known as *Impatiens hawkeri* and hereinafter referred to by the name 'Tamar Orange Orchid'.

The new *Impatiens* is a product of a planned breeding program conducted by the Inventor in De Lier, The Netherlands. The objective of the breeding program is to create new freely-branching New Guinea *Impatiens* cultivars with freely flowering habit and large attractive flowers.

The new *Impatiens* originated from a cross-pollination made by the Inventor in 2002 in De Lier, The Netherlands of an unnamed proprietary selection of *Impatiens hawkeri,* not patented, as the female, or seed, parent with the *Impatiens hawkeri* cultivar Paradise Tamana, not patented, as the male, or pollen, parent. The new *Impatiens* was discovered and selected by the Inventor as a single flowering plant within the progeny of the stated cross-pollination in a controlled environment in De Lier, The Netherlands in 2003.

Asexual reproduction of the new *Impatiens* by terminal cuttings in a controlled environment in De Lier, The Netherlands since 2003, has shown that the unique features of this new *Impatiens* are stable and reproduced true to type in successive generations.

SUMMARY OF THE INVENTION

The cultivar Tamar Orange Orchid has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Tamar Orange Orchid'. These characteristics in combination distinguish 'Tamar Orange Orchid' as a new and distinct cultivar of *Impatiens:*

1. Upright and outwardly spreading growth habit; mounded plant form.
2. Freely branching habit.
3. Dark green-colored leaves.
4. Freely flowering habit.
5. Large dark orange and light pink bi-colored flowers.
6. Good garden performance.

Plants of the new *Impatiens* can be compared to plants of the female parent selection. Plants of the new *Impatiens* differ from plants of the female parent selection in the following characteristics:

1. Plants of the new *Impatiens* are more vigorous and larger than plants of the female parent selection.
2. Plants of the new *Impatiens* have larger flowers than plants of the female parent selection.

Plants of the new *Impatiens* can be compared to plants of the male parent, the cultivar Paradise Tamana. Plants of the new *Impatiens* differ from plants of the cultivar Paradise Tamana in the following characteristics:

1. Plants of the new *Impatiens* are more vigorous and larger than plants of the cultivar Paradise Tamana.
2. Plants of the new *Impatiens* have larger leaves than plants of the cultivar Paradise Tamana.

Plants of the new *Impatiens* can be compared to plants of the *Impatiens* cultivar Paradise Amoya, not patented. In side-by-side comparisons conducted in De Lier, The Netherlands, plants of the new *Impatiens* differed from plants of the cultivar Paradise Amoya in the following characteristics:

1. Plants of the new *Impatiens* had more upright leaves than plants of the cultivar Paradise Amoya.
2. Plants of the new *Impatiens* and the cultivar Paradise Amoya differed in flower color.

BRIEF DESCRIPTION OF THE PHOTOGRAPHS

The accompanying colored photographs illustrate the overall appearance of the new *Impatiens,* showing the colors as true as it is reasonably possible to obtain in colored reproductions of this type. Colors in the photographs may differ slightly from the color values cited in the detailed botanical description which accurately describe the colors of the new *Impatiens*.

The photograph on the first sheet comprises a top perspective view of a typical flowering plant of 'Tamar Orange Orchid' grown in a container.

The photograph on the second sheet is a close-up view of typical flowers of 'Tamar Orange Orchid'.

DETAILED BOTANICAL DESCRIPTION

The aforementioned photographs and following observations, measurements and values describe plants grown in De Lier, The Netherlands, in 12-cm containers and under commercial practice during the summer in a glass-covered greenhouse with day and night temperatures averaging 18° C. Rooted young plants had been growing for about ten weeks when the photographs and description were taken. In the following description, color references are made to The Royal Horticultural Society Colour Chart, 1995 Edition, except where general terms of ordinary dictionary significance are used.

Botanical classification: *Impatiens hawkeri* cultivar Tamar Orange Orchid.

Parentage:

*Female, or seed, parent.*—Unnamed proprietary selection of *Impatiens hawkeri,* not patented.

*Male, or pollen, parent.*—*Impatiens hawkeri* cultivar Paradise Tamana, not patented.

Propagation:

*Type.*—By terminal cuttings.

*Time to initiate roots, summer.*—About five to seven days at temperatures of 19° C. to 20° C.

*Time to initiate roots, winter.*—About six to eight days at temperatures of 19° C. to 20° C.

*Time to produce a rooted young plant, summer.*—About 14 to 19 days at temperatures of 19° C. to 20° C.

*Time to produce a rooted young plant, winter.*—About 14 to 21 days at temperatures of 19° C. to 20° C.

*Root description.*—Fine; white to brown in color.

*Rooting habit.*—Freely branching.

Plant description:

*Plant and growth habit.*—Upright and outwardly spreading growth habit; mounded plant form. Freely branching habit with about seven lateral branches; pinching is typically not required. Moderately vigorous growth habit.

*Plant height.*—About 26 cm.

*Plant diameter.*—About 39 cm.

Lateral branch description:

*Length.*—About 18 cm.

*Diameter.*—About 1 cm.

*Internode length.*—About 5 cm.

*Strength.*—Moderately strong.

*Aspect.*—Initially upright to outwardly spreading.

*Texture.*—Smooth, glabrous; slightly glossy in luster.

*Color.*—146C tinted with 178A.

Foliage description:

*Arrangement.*—Opposite or in whorls of about five; simple.

*Length.*—About 10.5 cm.

*Width.*—About 4.5 cm.

*Shape.*—Elliptic.

*Apex.*—Acute.

*Base.*—Attenuate.

*Margin.*—Serrate with ciliation.

*Texture, upper and lower surfaces.*—Smooth, glabrous; leathery; moderately glossy in luster.

*Venation pattern.*—Pinnate; arcuate.

*Color.*—Developing foliage, upper surface: 144A to 146A. Developing foliage, lower surface: 139C. Fully expanded foliage, upper surface: 147B; venation, 195B. Fully expanded foliage, lower surface: 139C; venation, 182B.

*Petiole.*—Length: About 3 cm. Diameter: About 3 mm. Texture, upper and lower surfaces: Smooth, glabrous. Color, upper surface: 195B. Color, lower surface: 182C to 182D.

Flower description:

*Flower type and flowering habit.*—Single rounded axillary flowers. Freely flowering habit; usually about twenty flowers develop per lateral branch. Flowers positioned above the foliage and typically face upright or outward. Flowers last about ten days under greenhouse conditions. Petals self-cleaning, gynoecium persistent. Flowers not fragrant.

*Natural flowering season.*—Year-round under greenhouse conditions. In the garden, flowering from spring until fall in The Netherlands. Plants begin flowering about nine weeks after planting.

*Flower size.*—Diameter: About 6 cm. Depth: About 1.8 cm.

*Flower buds.*—Length: About 1 cm. Diameter: About 8 mm. Shape: Ovoid; pointed. Color: Between 46A to 46B and 44C.

*Petals.*—Quantity/arrangement: Five per flower in a single whorl. Length, banner petal: About 2.5 cm. Length, lateral and lower petals: About 2.8 cm. Width, banner petal: About 5 cm. Width, lateral and lower petals: About 2.2 cm. Shape, banner petal: Roughly reniform. Shape, lateral and lower petals: Broadly obcordate. Apex: Emarginate. Base: Acute. Margin: Entire. Texture, upper and lower surfaces: Smooth, glabrous. Color: When opening, upper surface: 43B; towards the base, 49D. When opening, lower surface: 40D. Fully opened, upper surface: 43B; towards the center, 49C. Fully opened, lower surface: 43D.

*Sepals.*—Quantity/arrangement: Three; one modified into an elongated spur. Length: About 1.8 cm. Width: About 8 mm. Shape: Ovate. Apex: Apiculate. Base: Cuneate. Margin: Entire. Texture, upper and lower surfaces: Smooth, glabrous. Color, upper and lower surfaces: Towards the apex, 144B; towards the margins, 52D; towards the center, 55D. Spur length: About 4.5 cm. Spur diameter: At flower, about 1.5 mm; at apex, less than 1 mm. Spur texture: Smooth, glabrous. Spur color: 51A.

*Peduncles.*—Length: About 5.8 cm. Diameter: About 2 mm. Angle: About 45° from vertical. Strength: Moderately strong. Texture: Smooth, glabrous. Color: 177C.

*Reproductive organs.*—Stamens: Quantity: Five fused at anthers; filaments free. Anther length: About 2 mm. Anther color: 182D. Pollen amount: Scarce. Pollen color: 158D. Pistils: Quantity per flower: One. Pistil length: About 1 mm. Stigma shape: Rounded. Stigma color: 158C. Ovary color: 143A.

*Seed/fruit.*—Seed and fruit production have not been observed.

Disease/pest resistance: Plants of the new *Impatiens* have not been observed to be resistant to pathogens and pests common to New Guinea *Impatiens*.

Garden performance: Plants of the new *Impatiens* have been observed to have good garden performance and tolerate wind, rain and temperatures ranging from about 4° C. to about 35° C.

It is claimed:

1. A new and distinct *Impatiens* plant named 'Tamar Orange Orchid' as illustrated and described.

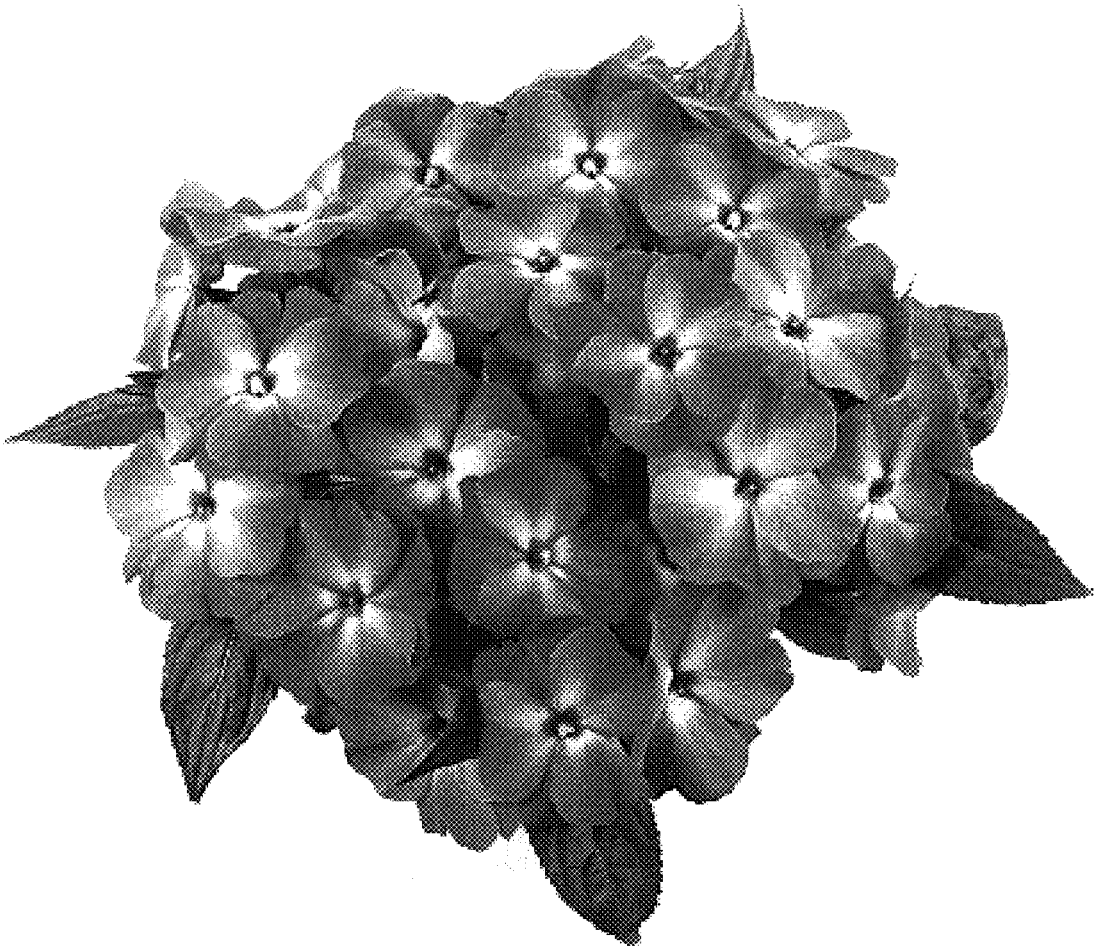

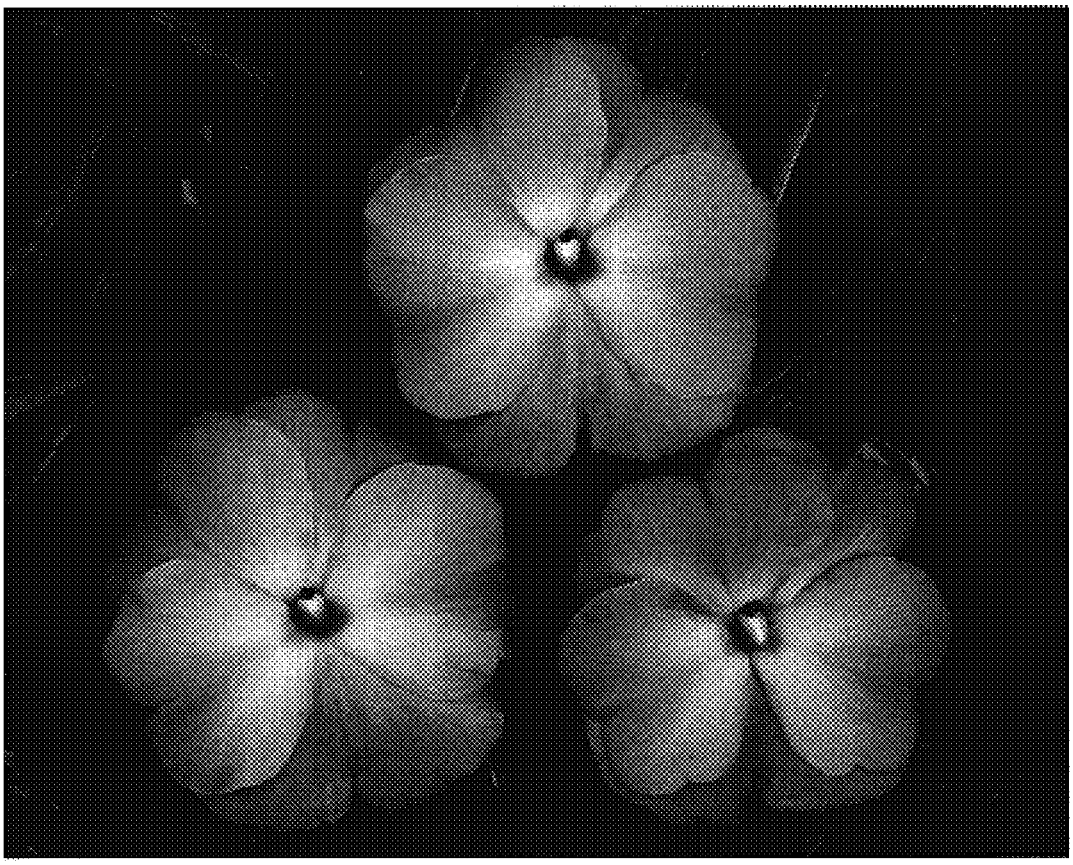

* * * * *